United States Patent [19]

Claren et al.

[11] Patent Number: 4,587,219

[45] Date of Patent: May 6, 1986

[54] DEVICE FOR MEASURING CONCENTRATION INCLUDING VALVE MEANS

[75] Inventors: Jan S. Claren; Lars-Goran Olsson, both of Lund, Sweden

[73] Assignee: Gambro Lundia AB, Sweden

[21] Appl. No.: 501,807

[22] Filed: Jun. 7, 1983

[30] Foreign Application Priority Data

Jun. 15, 1982 [SE] Sweden .............................. 8203696

[51] Int. Cl.⁴ .......................... C12M 1/40; C12M 1/34; C12M 1/12; B01L 11/00
[52] U.S. Cl. ..................................... 435/288; 435/291; 435/311; 137/625.46; 422/68; 422/103
[58] Field of Search ........................ 435/291, 288, 311; 422/101, 103, 68; 137/625.46, 625.15

[56] References Cited

U.S. PATENT DOCUMENTS

| | | | |
|---|---|---|---|
| 3,542,071 | 11/1970 | Lightner et al. | 137/625.46 |
| 3,626,938 | 12/1971 | Versaci . | |
| 4,119,406 | 10/1978 | Clemens | 422/68 X |
| 4,120,661 | 10/1978 | Naone | 422/68 |
| 4,123,353 | 10/1978 | Hakansson et al. | 435/14 |
| 4,152,391 | 5/1979 | Cabrera . | |
| 4,153,513 | 5/1979 | Edelmann et al. | 435/288 X |
| 4,229,542 | 10/1980 | Nylen et al. | 435/291 |
| 4,266,021 | 5/1981 | Nylen et al. | 435/14 |
| 4,298,026 | 11/1981 | Ambers . | |

FOREIGN PATENT DOCUMENTS

| | | | |
|---|---|---|---|
| 1933846 | 1/1970 | Fed. Rep. of Germany | 422/103 |
| 2853897 | 6/1979 | Fed. Rep. of Germany . | |
| 1564788 | 4/1980 | United Kingdom . | |

*Primary Examiner*—Robert J. Warden
*Assistant Examiner*—Randall E. Deck
*Attorney, Agent, or Firm*—Lerner, David, Littenberg, Krumholz & Mentlik

[57] ABSTRACT

A device is disclosed for measuring the concentration of a component of a complex medium, including a dialyzer for separating at least a portion of the component into the dialysate from the complex medium, means for measuring the concentration of the component in the dialyzate, and valve means having a measurement position and calibration position for alternatingly directing the complex medium and a calibration solution, respectively, to the dialyzer so that a calibration of the measuring means can be achieved at intervals between measurements, with the dialyzer being in fluid communication with the measuring means so that the dialyzate from the dialyzer is directed to the measuring means for measuring the concentration of the component in the dialyzate. The device also preferably includes an enzyme reactor.

17 Claims, 6 Drawing Figures

"DEVICE FOR MEASURING CONCENTRATION INCLUDING VALVE MEANS

BACKGROUND OF THE INVENTION

This invention relates to a device for measuring of the concentration of a component, e.g., glucose, of a complex medium, e.g., blood of a patient.

Devices for measuring of the concentration of glucose in blood are known through, inter alia, U.S. Pat. No. 4,229,542. Similar devices are described also in U.S. Pat. Nos. 4,123,353 and 4,266,021, and in British Pat. No. 1,564,788. The measuring procedure with these known devices comprises an initial calibration step, in which the measuring unit is calibrated against a standard solution (calibration solution) containing the component, e.g., glucose, in a known concentration. Thereafter, the concentration of the component in the complex medium is performed. For further information concerning this measuring procedure, reference is made to any of the above-mentioned patents.

A drawback with this known measuring procedure is that calibration is performable only at the beginning of each measurement. This means that after an initial calibration one must rely upon this calibration result during the whole measurement of the concentration of the component from the complex medium. This is of course undesirable, since the measuring unit (particularly, if it is a measuring electrode) easily can give rise to systematic deviations during the measurement depending on, for example, temperature disturbances or the like. It would be desirable to be able to perform calibration intermittently also during the measuring procedure in order to achieve a check of the accuracy of the measuring unit and thereby a safer measuring result.

SUMMARY OF THE INVENTION

According to the invention there is provided a device for measuring of the concentration of a component (e.g., a low molecular weight compound such as glucose) of a complex medium, e.g., blood for a patient. The device comprises a dialyzer for separating at least a portion of the component into the dialysate from the complex medium, means for measuring the concentration of the component in said dialysate, and valve means having a measurement position and calibration position for alternatingly directing the complex medium and a calibration solution, respectively, to the dialyzer so that a calibration of the measuring means can be achieved at intervals between measurements, wherein the dialyzer is in fluid communication with the measuring means so that the dialysate from the dialyzer is directed to said measuring means for measuring the concentration of the component in the dialysate. The device can also include an enzyme reactor in fluid communication with the dialyzer and the measuring means so that the dialysate from the dialyzer passes through the enzyme reactor to the measuring means, wherein the enzyme reactor is capable of enzymatically decomposing the component into smaller molecular weight compounds to be measured by the measuring means as an indirect measure of the concentration of the component.

DETAILED DESCRIPTION OF THE DRAWINGS

Figure 1:
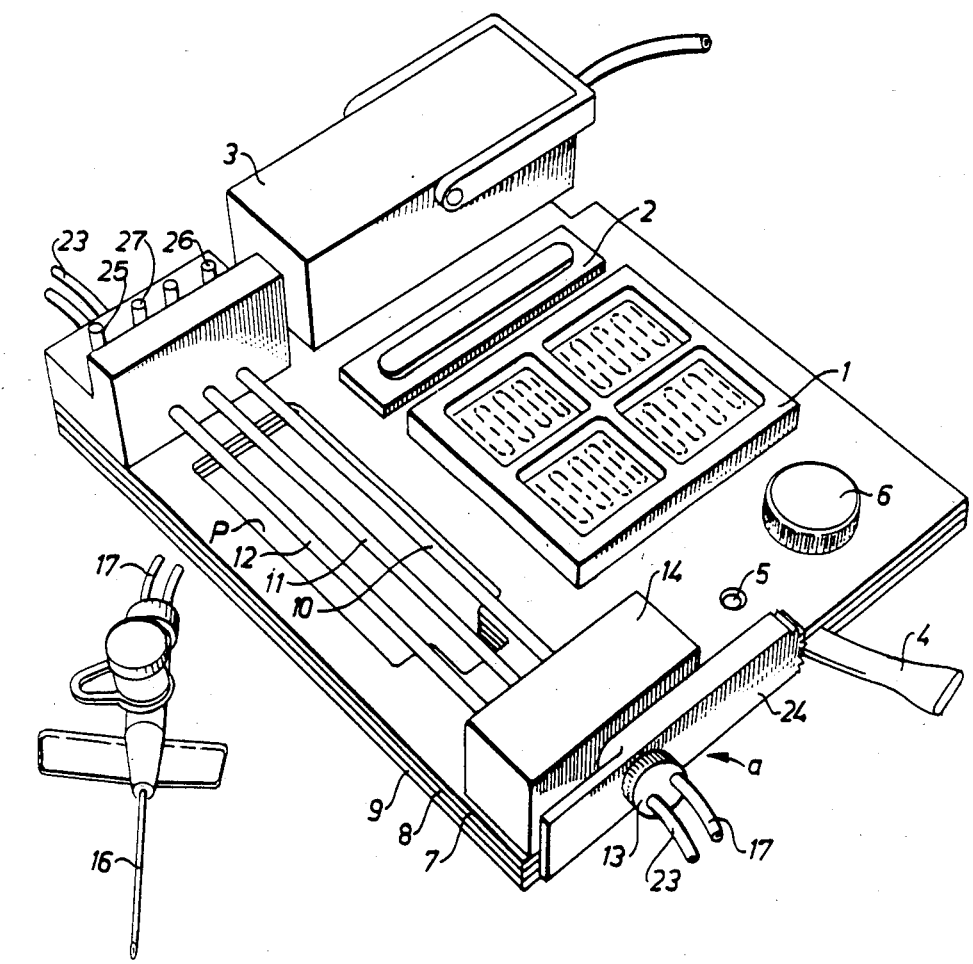
FIG. 1 shows a top perspective view of a preferred embodiment of a device in accordance with the present invention.

As is shown in FIG. 1, the device according to the present invention comprises preferably a dialyzer 1, an enzyme reactor 2, a measuring unit 3, a temperature sensor 4, a deaerator 5, and a flow changing device 6. These elements are conventional and are known to those of ordinary skill in this art and will therefore not be described in detail herein. For further information reference is instead made to any of the patents mentioned in the "BACKGROUND OF THE INVENTION" above, the disclosures of which are incorporated herein by reference as illustrations of such elements.

As is shown in FIG. 1, said elements are preferably arranged on the top side of a stack of plates 7, 8, 9 and are in communication with each other through a channel system. An example of a preferred channel system may be the channel system as described in U.S. patent application Ser. No. 501,808 filed June 7, 1983 entitled "Device For Measuring Of Concentration" in the names of Jan Seivert Claren, Lars-Goran Olsson and Birger Ragnar Hallberg, which corresponds to Swedish Patent Application No. 82.03695-5, filed June 15, 1982 in Sweden, the disclosures of which are incorporated herein by reference. Briefly, this channel system is composed of channels being formed between the stacked plates and a part of which is shown in FIG. 1 in the form of tubes 10, 11, and 12 which are arranged over a pump hole P through the plates to thereby provide a means for pumping the individual liquids in the channel system.

From FIG. 1 it can be seen that the present device also includes a valving means (designated "a" in FIG. 1) which will be described in more detail below with reference to FIGS. 2-6.

The valving means preferably comprises a valve piece 13, which is movable between two positions, namely, a calibration position and a measurement position. It preferably includes a stationary or fixed part 14, whereby the movable valve part 13 with its one end 13a is conveniently releasably attached to a corresponding end 14a of the fixed valve part 14.

The movable valve part 13 comprises an openable and closable inlet channel 15 for the complex medium, for example blood, which is adapted to be withdrawn from a patient by means of a cannula 16 and tube 17. The inlet channel 15 is in turn connectable to the dialyzer 1 via a corresponding outlet channel 18 in the fixed valve part 14 and the channel system not shown between the plates 10, 11 and 12 as described in our U.S.

patent application Ser. No. 501,808 filed June 7, 1983, which corresponds to Swedish Patent Application No. 82.03695-5 filed June 15, 1982 in Sweden, as discussed above.

The fixed valve part 14 comprises an inlet channel 19 for calibration solution, whereby the inlet channel 19 is directly connectable to the outlet channel 18 via a groove 20 formed in the end 13a of the movable valve part 13, when the valve means is in its calibration position as will be described in the following.

Furthermore, the fixed valve part 14 preferably comprises an inlet channel 21 for anticoagulant. This inlet channel 21 is directly connectable to the outlet channel 18 via said groove 20 of the movable valve part 13 when the valve means is in the calibration position, and is indirectly connectable to the outlet channel 18 via a corresponding channel 22 of the movable valve part 13 and a tube 23 which via a cannula 16 is in communication with the tube 17 for the complex medium and consequently, the inlet channel 15 in the movable valve part 13, as mentioned above.

The respective source for calibration solution and anticoagulant may, for example, be the container which is described in now abandoned U.S. patent application Ser. No. 392,248 filed June 25, 1982 entitled "Apparatus For Measuring The Concentration Of Low Molecular Weight Compounds In Complex Media Including Compartmentalized Container Therefor", which corresponds to Swedish Patent Application No. 81.04146-9 filed July 3, 1981 in Sweden, the diclosures of which are incorporated hereby by reference. The container can be in communication with the channel system in the plates 7, 8, 9 in the manner as described in our U.S. patent application Ser. No. 501,808 filed June 7, 1983 which corresponds to Swedish Patent Application No. 82.03695-5 as discussed above. Preferably, this container is provided with a level marking of the kind as described in now abandoned U.S. patent application Ser. No. 392,293 filed June 25, 1982 entitled "Containers Including Readily Observable Fluid Level Indicators", which corresponds to Swedish Patent Application No. 81.04147-7 filed July 3, 1981 in Sweden, the disclosures of which are incorporated hereby by reference.

Operation Of The Devices

A. CALIBRATION

Figure 2:
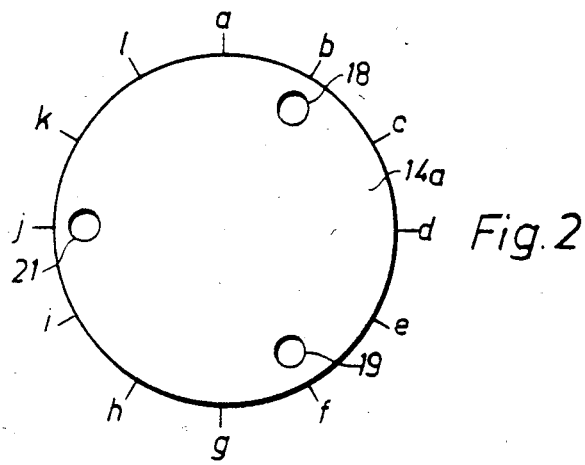
FIG. 2 illustrates a top view of a fixed part of a valve means in accordance with the present invention.
Figure 3:
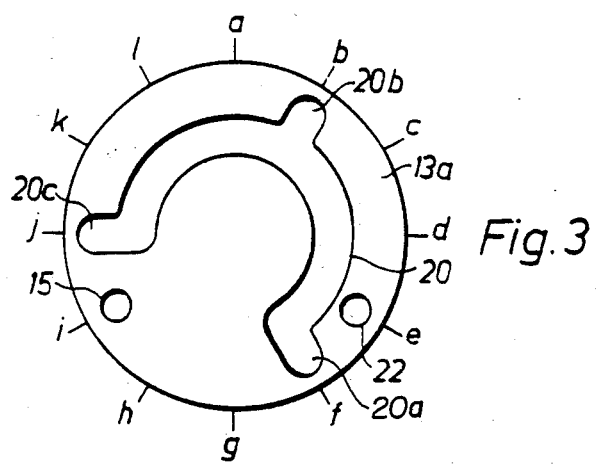
FIG. 3 illustrates a top view of a movable part of a valve means in accordance with the present invention when said valve means is in the calibration position.

When calibration is to be performed with the device according to the invention the valving means is set, preferably by means of an arm 24, in the position as shown in FIGS. 2 and 3. As is shown in these figures, the inlet channel 19 for calibration solution in the fixed valve part 14 is in communication with the groove 20 at expanded portion 20a and, via this groove, is in communication at expanded portion 20b with the outlet channel 18 in the fixed valve part 14. The outlet channel 18, as described, is in communication with the dialyzer 1 via the channel system between the plates 7, 8 and 9. An inlet channel 21, e.g., for anticoagulant, in the fixed valve part 14 is in communication with the groove 20 at expanded portion 20c and, via this groove, is in communication at expanded portion 20b with the outlet channel 18. Furthermore, it can be seen from FIGS. 2 and 3 that the communication between the inlet channel 15 for the complex medium in the movable valve part 13 and the outlet channel 18 is interrupted. The communication between the inlet channel 21, e.g., for anticoagulant, in the fixed valve part 14 and the corresponding channel 22 in the movable valve part 13 is also interrupted.

During calibration, the calibration solution will thus be pumped from a source (not shown) in communication with an inlet 25 and through the channel system between the plates 7, 8 and 9 into the inlet channel 19 in the fixed valve part 14 and via the expanded portion 20a, groove 20, and expanded portion 20b in the movable valve part 13 into the outlet channel 18 in the fixed valve part 14 and from this outlet channel 18 via the channel system between the plates 7, 8 and 9 to the dialyzer 1. From the dialyzer the calibration solution is then pumped via the channel system to a waste container (not shown) in communication with an outlet 26 in the manner as described in our U.S. patent application Ser. No. 501,408 filed June 7, 1983, which corresponds to Swedish Patent Application No. 82.03695-5 filed June 15, 1982 in Sweden as discussed above. Simultaneously, anticoagulant can be pumped from a source (not shown) in communication with an inlet 27 through the tube 12 into the inlet channel 21 in the fixed valve part 14 and from this channel 21 to the outlet 18 via the expanded portion 20c, groove 20, and expanded portion 20b and from the outlet channel 18 through the same channel system as the calibration solution. By the above apparatus, mixing of anticoagulant and calibration solution is obtained when these two flows meet in the groove 20 and expanded portion 20b.

B. CONCENTRATION MEASUREMENT

Figure 4:
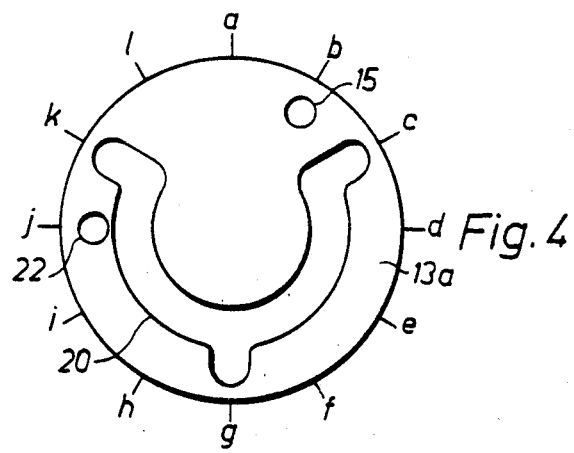
FIG. 4 illustrates a top view of a movable part of a valve means in accordance with the present invention when said valve means is in the measurement position.
Figure 5:
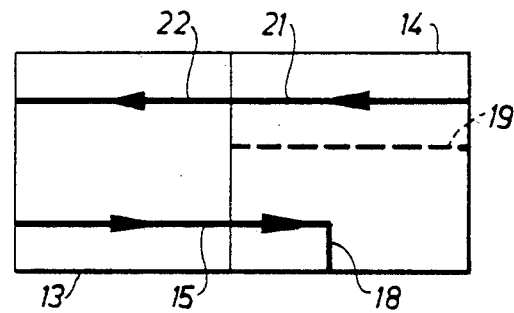
FIG. 5 illustrates schematically a side view of a fixed part and a movable part of a valve means in accordance with the present invention when said valve means is in its measurement position.
Figure 6:
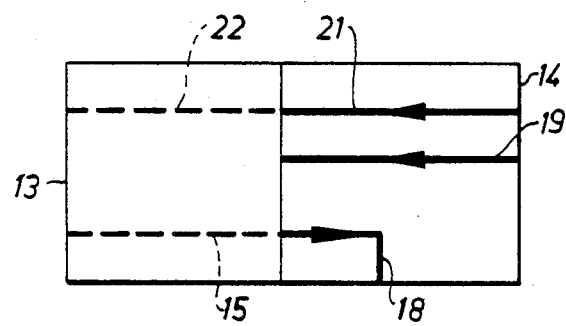
FIG. 6 illustrates schematically a side view of a fixed part and a movable part of a valve means in accordance with the present invention when said valve means in in the calibration position.

During concentration measurement of the component of the complex medium (e.g., blood), which component is usually a low molecular weight compound (for example glucose), the valve means is set in the position as shown in FIGS. 2 and 4, and 5, respectively. In this position, the inlet channel 15 for the blood in the movable valve part 13 is in direct communication with the outlet channel 18 in the fixed valve part 14 and, as described above, in communication with the dialyzer 1 via the channel system (not shown) between the plates 7, 8 and 9. Furthermore, in this position the inlet channel 21, e.g., for anticoagulant, in the fixed valve part 14 is in communication with the outlet channel 18 via the corresponding channel 22 in the movable valve part 13, the tube 23, the cannula 16, the tube 17 and the inlet channel 15 in the movable valve part 13 for the complex media. In this position, the direct communication between the inlet channel 21 in the fixed valve part 14 and the outlet channel 18 is interrupted as is the communication between the inlet channel 19 for calibration solution in the fixed valve part 14 and the outlet channel 18.

During concentration measurement of the component, the complex medium, e.g., blood, is thus withdrawn from, for example, a patient through the cannula 16 and pumped to the dialyzer 1 via the tube 17, inlet channel 15 in the movable valve part 13, the outlet channel 18 in the fixed valve part 14 and the channel system (not shown) between the plates 7, 8 and 9 in the manner as described in our U.S. patent application Ser. No. 501,808 filed June 7, 1983, which corresponds to Swedish Patent Application No. 8203695-5 filed June 15, 1982 as discussed above. Simultaneously, anticoagulant is pumped into the inlet channel 21 in the fixed valve part 14 in the manner as described above and to the cannula 16 via the corresponding channel 22 in the movable valve part 13 and the tube 23. From the cannula 16, the anticoagulant will then follow the same flow pathway as the complex medium. Mixing of anticoagulant and blood within the cannula 16 is thereby provided where these two flows meet.

From the above description it is apparent that, by means of the present device, it is possible at intervals during the measurement of the component of in the complex medium to calibrate the measuring unit 3 by simply setting the valve means 13 in its two respective positions for calibration and measuring.

The risk of coagulation in the cannula 16 and tube 17 during the calibration, i.e., when these two elements are filled with, for example, blood which then is quiescent, is avoided by the fact that the blood simultaneously and continuously is mixed with anticoagulant which thus meets the blood flow within the cannula 16.

A further essential advantage which is achieved according to the invention is that the tube 23 does not necessarily have to be disconnected from the cannula 16 during the calibration, which is particularly accentuated in cases where especially long cannulas are used. According to the invention, it is thus possible to maintain the tube 23 for anticoagulant in communication with the cannula 16 during the whole measuring procedure.

The device of the present invention can also be used in quantitative and/or qualitative determination of low molecular weight compounds in other complex media than blood, for example, microbiological culturing chambers.

It will be understood tht the embodiments described herein are merely exemplary and that a person skilled in the art may make many variations and modification without departing from the scope of the invention. All such modifications and variations are intended to be included within the scope of the invention as defined in the appended claims.

What is claimed is:

1. A device for measuring the concentration of a component of a complex medium, comprising a dialyzer for separating at least a portion of said component into the dialysate from said complex medium, means for measuring the concentration of said component in said dialysate, and valve means having a measurement position and calibration position for alternatingly directing the complex medium and a calibration solution, respectively, through a common outlet channel to the dialyzer, said valve means comprising a movable valve part including an openable and closable first inlet channel for the complex medium, said movable valve part being movable between two positions corresponding to said measurement position and said calibration position, a fixed valve part including an openable and closable second inlet channel for the calibration solution, and said common outlet channel so that a calibration of the measuring means can be achieved at intervals between measurements, said dialyzer being in fluid communication with said measuring means so that the dialysate from the dialyzer is directed to said measuring means for measuring the concentration of said component in said dialysate.

2. A device according to claim 1 further comprising an enzyme reactor in fluid communication with said dialyzer and said measuring means so that the dialysate from said dialyzer passes through the enzyme reactor to said measuring means, said enzyme reactor being capable of enzymatically decomposing said component into smaller molecular weight compounds to be measured by said measuring means as an indirect measure of the concentration of said component.

3. A device according to claim 1, wherein the valve means further comprises a third inlet channel which is alternatingly directly and indirectly connectable to the common outlet channel.

4. A device according to claim 3, wherein the third inlet channel is arranged in said fixed valve part.

5. A device according to claim 3, wherein the third inlet channel is indirectly connectable to the common outlet channel via an openable and closable channel in said movable valve part in communication with said first inlet channel for the complex medium when said valve means is in its measurement position.

6. A device according to claim 3, wherein said third inlet channel is in fluid communication with said common outlet channel when said valve means is in a measurement position and when said valve means is in a calibration position.

7. A device according to claim 3, wherein one surface of said movable valve part is releasably attached to a corresponding surface of said fixed valve part.

8. A device according to claim 7, wherein said third inlet channel is directly connectable to the common outlet channel via a groove in said one surface of said movable valve part when said valve means is in its calibration position.

9. A device according to claim 8, wherein said third inlet channel in said fixed valve part and said first inlet channel for the complex medium in the movable valve part are simultaneously in communication with said common outlet channel when said movable valve part is in its measurement position, and wherein said third inlet channel and said second inlet channel for calibration solution are simultaneously in communication with said common outlet channel via said groove in said movable valve part when said movable valve part is in its calibration position, whereby the fluid communication between said first inlet channel for the complex medium and said outlet channel is interrupted.

10. A device according to claim 9, wherein said movable valve part is movable between its two positions by means of an arm provided on the movable valve part.

11. A device for measuring the concentration of a component of a complex medium, comprising a dialyzer for separating at least a portion of said component into the dialysate from said complex medium, means for measuring the concentration of said component in said dialysate, and valve means having a measurement position and calibration position for alternatingly directing the complex medium and a calibration solution, respectively, through a common outlet channel to the dialyzer, said valve means comprising a movable valve part including an openable and closable first inlet channel for the complex medium, said movable valve part being movable between two positions corresponding to said measurement position and said calibration position, a fixed valve part including an openable and closable second inlet channel for the calibration solution, said common outlet channel, and a third inlet channel which is alternatingly directly and indirectly connectable to said common outlet channel, whereby a calibration of the measuring means can be achieved at intervals between measurements, said dialyzer being in fluid communication with said measuring means so that the dialysate from the dialyzer is directed to said measuring means for measuring the concentration of said component in said dialysate.

12. A device according to claim 11 wherein said fixed valve part includes said third inlet whereby said third inlet channel is directly connected to said common outlet channel when said valve means is in said calibration position, and said third inlet channel is indirectly connected to said common outlet channel when said valve means is in said measurement position.

13. A device according to claim 12 wherein said movable valve part includes an openable and closable channel, whereby said channel is opened when said valve is in said measurement position so as to indirectly connect said third inlet channel to said common outlet channel, and said channel is closed when said valve means is in said calibration position.

14. A device according to claim 13 wherein one surface of said movable valve part is releasably attached to a corresponding surface of said valve part.

15. A device according to claim 14 wherein said movable valve part includes groove means for directly connecting said third inlet channel to said common outlet channel when said valve means is in said calibration position.

16. A device according to claim 15 wherein said groove means in said movable valve part also connects said second inlet channel for said calibration solution with said common outlet channel when said movable valve part is in said calibration position.

17. A device according to claim 16 wherein said movable valve part includes an arm to facilitate movement of said movable valve part between said measurement and calibration positions.

* * * * *

UNITED STATES PATENT AND TRADEMARK OFFICE
CERTIFICATE OF CORRECTION

PATENT NO. : 4,587,219

DATED : May 6, 1986

INVENTOR(S) : Jan S. Claren; Lars-Goran Olsson

It is certified that error appears in the above-identified patent and that said Letters Patent is hereby corrected as shown below:

Column 7, line 15, after "said" and before "valve", insert --fixed--.

Signed and Sealed this

Twenty-sixth Day of August 1986

[SEAL]

Attest:

DONALD J. QUIGG

Attesting Officer

Commissioner of Patents and Trademarks